United States Patent
Peterson

(10) Patent No.: US 6,315,759 B1
(45) Date of Patent: Nov. 13, 2001

(54) PROTECTIVE COVER FOR INTRAVENOUS LINES AND OTHER ELONGATED MEMBERS

(76) Inventor: Travis Peterson, 2232 Fuller Ct., #105A, Ann Arbor, MI (US) 48103

(*) Notice: Subject to any disclaimer, the term of this patent is extended or adjusted under 35 U.S.C. 154(b) by 0 days.

(21) Appl. No.: 09/468,630

(22) Filed: Dec. 21, 1999

(51) Int. Cl.$^7$ .................................................. A61M 5/00
(52) U.S. Cl. ........................ 604/171; 428/36.5; 248/68.1
(58) Field of Search ................. 604/80–82, 171, 604/174, 179, 189; 285/45, 47; 428/36.5, 36.9; 248/49, 68.1

(56) References Cited

U.S. PATENT DOCUMENTS

| | | | |
|---|---|---|---|
| 4,748,060 | * 5/1988 | Fry et al. | 428/36 |
| 4,795,429 | 1/1989 | Feldstein | 604/80 |
| 4,971,271 | * 11/1990 | Sularz | 248/68.1 |
| 4,988,062 | 1/1991 | London | 248/68.1 |
| 5,224,674 | 7/1993 | Simons | 248/68.1 |
| 5,226,892 | * 7/1993 | Boswell | 604/180 |
| 5,336,179 | 8/1994 | Ryan | 604/80 |
| 5,427,849 | * 6/1995 | McClintock et al. | 428/353 |
| 5,601,894 | * 2/1997 | Maruschak | 428/35.9 |
| 5,709,665 | * 1/1998 | Vergano et al. | 604/174 |
| 5,735,821 | * 4/1998 | Dobkin | 604/174 |
| 5,783,274 | * 7/1998 | Knittel et al. | 428/36.9 |
| 5,876,371 | 3/1999 | Yokoyama et al. | 604/80 |
| 5,964,252 | * 10/1999 | Simmons et al. | 138/149 |
| 5,997,967 | * 12/1999 | Hawkings | 428/34.9 |

* cited by examiner

Primary Examiner—Sharon Kennedy

(57) ABSTRACT

A protective cover is used to surround one or more elongated members such as a plurality of intravenous lines. In alternative embodiments, the cover may be used to cover or protect baby crib rails, bicycle frame sections, handles and other items. The cover preferably assumes the form of a generally cylindrical hollow tube composed of a flexible, resilient material such as closed-cell foam. The tube includes a slit running lengthwise down the tube, enabling the tube to be placed around and over the elongated member by spreading the slit to expose a pair of adjacent, opposing surfaces, each with a length equal to the length of the tube and a width equal to the thickness of the wall. The tube preferably further includes means, other than the tube itself, for maintaining the tube in position around the member. In one configuration, the means for maintaining the tube in position around the member includes an adhesive on one or both of the opposing surfaces, which may be covered with a release layer to expose the adhesive. A separate release layer may be used to cover the slit as well. The means for maintaining the tube in position around the member may also include at least one elongated adhesive strip disposed on the inner wall of the tube. When used to cover and protect intravenous lines, the release layer covering the slit, or a portion of the outer wall covered by the release layer may include one or more messages concerning the use or re-use of the cover.

19 Claims, 1 Drawing Sheet

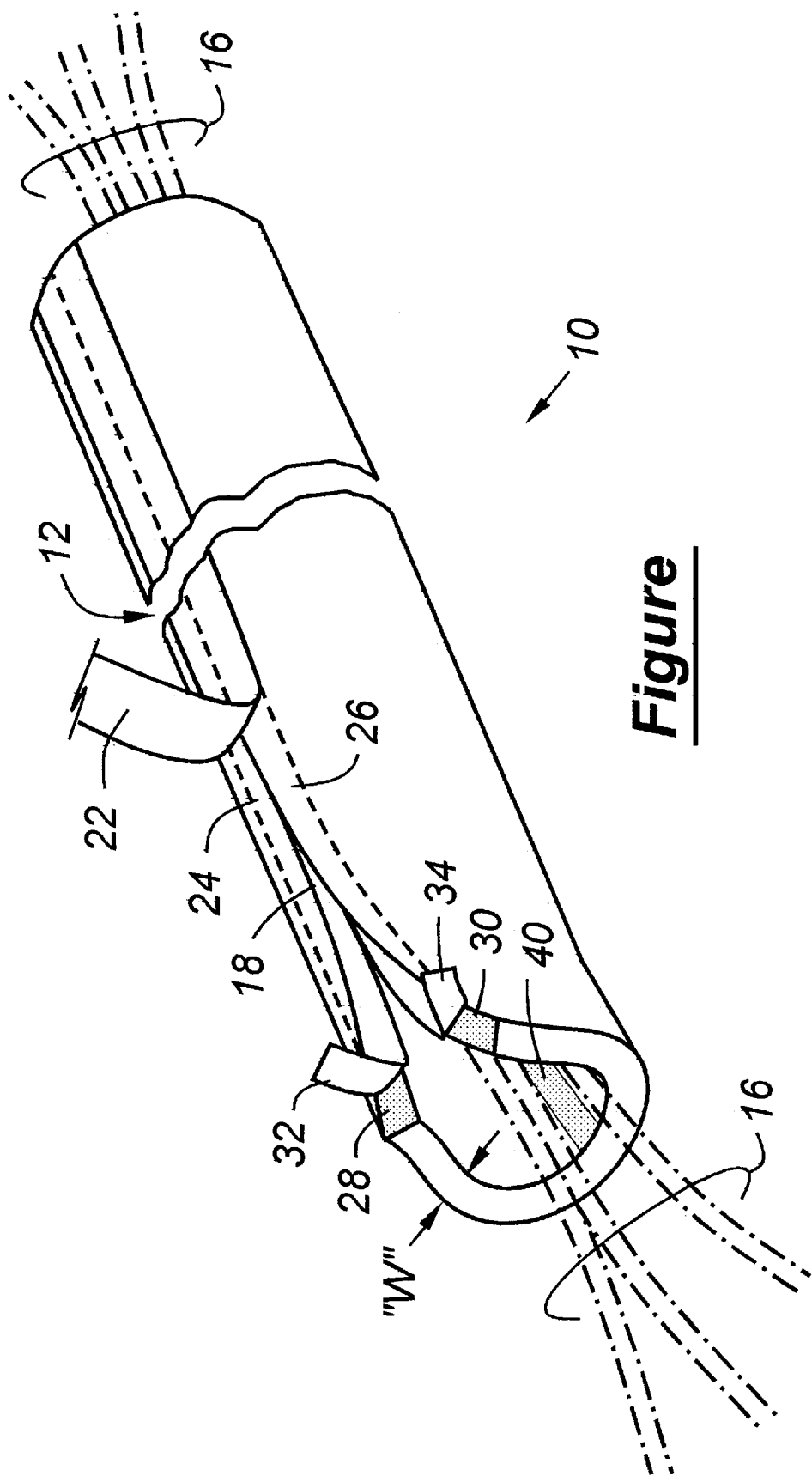

PROTECTIVE COVER FOR INTRAVENOUS LINES AND OTHER ELONGATED MEMBERS

FIELD OF THE INVENTION

This invention relates generally to protective covers and hospital appliances, and, more particularly, to a simple but effective cover that may be used to organize and protect intravenous lines and other types of tubing and electrical connections to bedridden patients.

BACKGROUND OF THE INVENTION

During certain medical procedures and hospitalization, patients are often connected to multiple devices and fluid sources for the purposes of monitoring, providing medications, and so forth. Such lines are interfaced to the patient's body through catheters, intravenous and fluid lines, EKG signal lines, and other types of tubing. Many of these lines and tubes are connected to the patient during transport, and have a tendency to become entangled and confused. Also, particularly when turning comers, and so forth, through more narrow hospital corridors or past other patients having similar connections, there is a risk that lines will be disturbed or even disconnected if caught on a projection. A mass of entangled lines and tubes also gives family members and loved ones anxious feelings when seeing a patient treated in this manner.

There have been several proposals to arrange intravenous lines, and the like, but thus far all such proposals have been intended to label rather than protect the various/signal carrying conduits. Examples include U.S. Pat. Nos. 4,795,429; 4,988,062; 5,224,674; 5,336,179; and 5,876,371. Using the latter of these as representative, an intravenous tube holder for use in a trauma unit or similar environment, includes an element having a plurality of tracks, each designed to secure an intravenous tube and writing surface next to each track to identify content and/or dosage information. Each element has a male extension and female indent for interconnecting additional elements to accommodate a greater number of intravenous tubes.

Although mechanisms of this kind help with labeling and identifying various lines, they do nothing to protect these tubes and wires lengthwise from becoming overly entangled and caught up on projections or other articles during transport. The need therefore remains for a simple but effective means to both organize and protect intravenous lines and tubes to ensure a tidy yet functional arrangement.

SUMMARY OF THE INVENTION

This invention resides in a protective cover for surrounding at least one elongated member. In the preferred embodiment, the cover is used to protect a plurality of intravenous lines. However, in alternative embodiments, other members such as baby crib rails, bicycle frame sections, handles and other items may be covered.

Broadly, the invention assumes the form of a generally cylindrical hollow tube composed of a flexible, resilient material such as closed-cell foam. The tube has a length, an outer wall having and outer diameter, an inner wall having an inner diameter, a wall thickness. The tube further includes a slit running lengthwise down the tube, enabling the tube to be placed around and over the elongated member by spreading the slit to expose a pair of adjacent, opposing surfaces, each with a length equal to the length of the tube and a width equal to the thickness of the wall.

The tube preferably further includes means, other than the tube itself, for maintaining the tube in position around the member. In one configuration, the means for maintaining the tube in position around the member includes an adhesive on one or both of the opposing surfaces, which may be covered with a release layer to expose the adhesive. A separate release layer may be used to cover the slit as well.

When used to cover and protect intravenous lines, the release layer covering the slit may further include a message concerning the use or re-use of the cover. A message concerning the use or re-use of the cover may also be provided on the outer wall of the tube which is exposed when the release layer covering the slit is removed.

The means for maintaining the tube in position around the member may also include at least one elongated adhesive strip disposed on the inner wall of the tube. This adhesive may be used apart from, or together with, the adhesive used to close the slit upon positioning around the member. According to a method aspect of the invention, with the adhesive strip disposed lengthwise along the inner wall of the tube, the tube may be pressed so that the adhesive strip makes contact with, and bonds to, the elongated member, thereby holding the tube in place.

BRIEF DESCRIPTION OF THE DRAWINGS

FIG. 1 is a drawing which shows, from an oblique perspective, a protective cover according to a preferred embodiment of the invention.

DETAILED DESCRIPTION OF THE INVENTION

Broadly, this invention solves the disadvantages of the prior art by providing an elongated flexible hollow sleeve, depicted in the figure as item 10. The sleeve 10 is preferably made of a flexible, soft resilient or "spongy" material such as a foam of the type used for pipe insulation and other purposes. The sleeve 10 is shown with a separation 12, to denote the fact that the sleeve may be provided in any convenient length, such as six inches, one foot, two feet, and so forth. The various lengths may be used as required, depending upon how many lines 16 need to be accommodated, and for what length. The thickness W may also be varied depending upon the circumstances to provide a desired level of protection and flexibility.

The sleeve 10 is enclosed around the lines 16 by providing a slit 18 lengthwise along the sleeve, as shown. Although nothing other than the slit itself is required in practicing the invention in its most basic form, in the preferred embodiment, a releasable layer 22 is provided over the slit, and this releasable layer serves at least the purpose of indicating to others that the sleeve has been used. For example, the layer 22 might be imprinted with a message such as "TEAR OFF TO USE." Preferably, the sleeve 10 would only be usable once, then throw away for reasons of sterilization in a typical hospital setting.

Also in the preferred embodiment, when the release layer 22 is lifted off the slit 18, a visual indication may be provided on either side of the slit, such as opposing areas 24 and 26, which may carry a message to indicate that the sleeve has been used, and that it should not be used again. For example, the wording "DO NOT REUSE" may be used or, alternatively, color schemes may be provided. For example, the release layer 22 may be green indicating that the sleeve can be used, whereas the elements 24 and 26, may be red, indicating that the sleeve has already been used and should not be used again. The opposing sides 24 and 26 may either be imprinted directly onto the material comprising the sleeve 10, or, alternatively, may be provided by a second tape layer which needs to be cut in order to open the sleeve or, alternatively, two separate pieces of tape which run lengthwise on either side of the slit 18.

The opposing surfaces 28 and 30 of the slit may be provided without any kind of adhesive. However, in the preferred embodiment, both halves incorporate an adhesive along with release layers 32 and 34, which, when removed, expose the adhesive layers 28 and 30, so that when the sleeve is wrapped around the lines 16, the adhesive layers interface to one another and form a bond, requiring more effort to remove the sleeve, and this additional effort, which may destroy at least a portion of the sleeve or the adhesive portions, could also be used as indicative of a sleeve that has already been used.

As a further option, an adhesive strip 40 may also be provided lengthwise inside the inner diameter of the sleeve 10 assist in holding one or more of the lines 16 against the inner side wall of the sleeve. In addition, particularly with the addition of internal adhesive layer 40 (which could also be provided with a release layer, the invention finds utility beyond intravenous line organization, and may be use to cover or protect elongated members such at top or other rails on baby cribs, handles for shopping carts and other implements, bicycle frame sections, and so forth.

I claim:

1. A protective cover for surrounding at least one elongated member, comprising:
   a generally cylindrical hollow tube composed of a flexible, resilient material, the tube having a length, an outer wall having an outer diameter, an inner wall having an inner diameter, and wherein the distance between the inner and outer walls defines a wall thickness;
   a slit running lengthwise down the tube, enabling the tube to be placed around and over the elongated member by spreading the slit to expose a pair of adjacent, opposing surfaces, each with a length equal to the length of the tube and a width equal to the wall thickness;
   a release layer covering the slit; and
   a message concerning the use or re-use of the cover, which is exposed when the release layer covering the slit is removed.

2. The protective cover of claim 1, further including an adhesive on one or both of the opposing surfaces.

3. The protective cover of claim 2, further including a release layer covering each surface having the adhesive.

4. The protective cover of claim 1, further including at least one elongated adhesive strip disposed on the inner wall of the tube.

5. The protective cover of claim 1, wherein the tube is adapted to surround a plurality of intravenous lines.

6. The protective cover of claim 1, wherein the flexible, resilient material is foam.

7. A protective cover for surrounding at least one line, comprising:
   a generally cylindrical hollow tube composed of a foam material, the tube having a length, an outer diameter, an inner diameter, and a wall thickness of essentially half the difference between the outer diameter and the inner diameter;
   a slit running lengthwise down the tube, enabling the tube to be placed around and over the elongated member by spreading the slit to expose a pair of adjacent, opposing surfaces, each with a length equal to the length of the tube and a width equal to the wall thickness;
   a release layer covering the slit;
   a visual indication to indicate use of the tube; and
   an adhesive on one or both of the opposing surfaces which is exposed with a separate release layer.

8. The protective cover of claim 7, wherein the visual indication comprises a message on the release layer concerning the use or re-use of the cover.

9. The protective cover of claim 7, wherein the visual indication comprises a message concerning the use or re-use of the cover which is exposed when the release layer covering the slit is removed.

10. The protective cover of claim 7, further including an adhesive strip provided inside the inner diameter of the tube.

11. A method of covering and protecting an intravenous line, comprising the steps of:
    providing a generally cylindrical hollow tube composed of a flexible, resilient material, the tube having a length, an outer diameter, an inner diameter, and a wall thickness, the tube further including a lengthwise slit through the wall to create a pair of adjacent, opposing surfaces, the tube further including at least one adhesive strip to hold the tube in place once positioned around the member, and a release layer covering the slit;
    removing the release layer;
    spreading the slit of the tube so as to substantially surround the intravenous line; and
    maintaining the tube in position around the member using the adhesive strip.

12. A method of claim 11, wherein the adhesive strip is disposed lengthwise along the inner wall of the tube, with the method further including the step of pressing the tube so that the adhesive strip makes contact with and bonds to the elongated member, thereby holding the tube in place.

13. A method of preventing the entanglement of a plurality of intravenous lines, comprising the steps of:
    providing a tube formed of a flexible resilient material having a lengthwise slit;
    spreading the slit of the tube so as to substantially surround the plurality of intravenous lines; and
    maintaining the tube in position around the plurality of intravenous lines using an adhesive strip.

14. The method of claim 13, wherein the flexible, resilient material is a foam a material.

15. A method of covering and protecting an intravenous line, comprising the steps of:
    providing a protective cover comprising:
       a generally cylindrical hollow tube composed of a wall of flexible, resilient material, the tube having a length, an outer diameter, an inner diameter, and a wall thickness, the tube further including a lengthwise slit through the wall to create a pair of adjacent, opposing surfaces;
       a primary release layer covering the slit;
       a message that is exposed when the primary release layer is removed;
       an adhesive on one or both of the opposing surfaces;
       a secondary release layer covering each surface having the adhesive; and
       a means for maintaining the tube in position around the intravenous line, the means comprising an elongated adhesive strip provided inside the inner diameter of the tube;
    removing the primary release layer to uncover the slit and expose the message;

spreading the slit in the tube;

inserting the intravenous line into the slit such that a portion of the intravenous line passes through the inner diameter of the tube;

closing the slit such that the opposing surfaces contact; and maintaining the tube in position around the intravenous line using the elongated adhesive strip.

16. The method according to claim 15, wherein a plurality of intravenous lines are covered and protected, the tube having an inner diameter large enough to accommodate the plurality of lines and the inserting step comprises inserting the plurality of intravenous lines into the slit.

17. The method according to claim 15, wherein the message concerns use or reuse of the cover.

18. The method according to claim 15, wherein the flexible resilient material is an opaque foam.

19. The method according to claim 15, wherein the tube has an inner surface and the elongated adhesive strip is disposed lengthwise on the inner surface.

* * * * *